(12) United States Patent
Duncan et al.

(10) Patent No.: US 7,507,868 B2
(45) Date of Patent: Mar. 24, 2009

(54) OLEFIN OLIGOMERIZATION PROCESS

(75) Inventors: Carolyn B. Duncan, Franklin, GA (US); Raphael Frans Caers, Edegem (BE); David W. Turner, Raymond, ME (US); Michael J. Keenan, Baton Rouge, LA (US); Ernest E. Green, Baton Rouge, LA (US); Ramzi Y. Saleh, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 777 days.

(21) Appl. No.: 10/509,530

(22) PCT Filed: Mar. 28, 2003

(86) PCT No.: PCT/US03/09733

§ 371 (c)(1),
(2), (4) Date: Sep. 24, 2004

(87) PCT Pub. No.: WO03/082781

PCT Pub. Date: Oct. 9, 2003

(65) Prior Publication Data

US 2005/0165250 A1    Jul. 28, 2005

Related U.S. Application Data

(60) Provisional application No. 60/368,927, filed on Mar. 29, 2002.

(51) Int. Cl.
*C07C 2/12* (2006.01)
(52) U.S. Cl. .................. 585/533; 585/520; 585/530; 585/532
(58) Field of Classification Search .......... 585/520, 585/530, 532, 533
See application file for complete search history.

(56) References Cited

U.S. PATENT DOCUMENTS

| | | | |
|---|---|---|---|
| 3,231,621 A | 1/1966 | Slaugh | 260/604 |
| 3,239,566 A | 3/1966 | Slaugh et al. | 260/604 |
| 3,239,569 A | 3/1966 | Slaugh et al. | 260/632 |
| 3,239,570 A | 3/1966 | Slaugh et al. | 260/632 |
| 3,239,571 A | 3/1966 | Slaugh et al. | 260/632 |
| 3,420,898 A | 1/1969 | Van Winkle et al. | 260/632 |
| 3,440,291 A | 4/1969 | Van Winkle et al. | 260/632 |
| 3,448,157 A | 6/1969 | Slaugh et al. | 260/604 |
| 3,448,158 A | 6/1969 | Slaugh et al. | 260/604 |
| 3,496,203 A | 2/1970 | Morris et al. | 260/439 |
| 3,496,204 A | 2/1970 | Morris et al. | 260/439 |
| 3,501,515 A | 3/1970 | Van Winkle et al. | 260/439 |
| 3,527,818 A | 9/1970 | Mason et al. | 260/632 |
| 3,960,978 A | 6/1976 | Givens et al. | 260/683.15 |
| 4,076,842 A | 2/1978 | Plank et al. | 423/328 |
| 4,150,062 A | 4/1979 | Garwood et al. | 260/673 |
| 4,211,640 A | 7/1980 | Garwood et al. | 208/255 |
| 4,227,992 A | 10/1980 | Garwood et al. | 208/46 |
| 4,298,547 A | 11/1981 | Young | 260/505 |
| 4,439,409 A | 3/1984 | Puppe et al. | 423/328 |
| 4,547,613 A | 10/1985 | Garwood et al. | 585/533 |
| 4,826,667 A | 5/1989 | Zones et al. | 423/277 |
| 4,855,527 A | 8/1989 | Page et al. | 585/527 |
| 4,870,038 A | 9/1989 | Page et al. | 502/62 |
| 4,954,325 A | 9/1990 | Rubin et al. | 423/328 |
| 5,026,933 A | 6/1991 | Blain et al. | 585/7 |
| 5,236,575 A | 8/1993 | Bennett et al. | 208/46 |
| 5,250,277 A | 10/1993 | Kresge et al. | 423/329.1 |
| 5,284,989 A | 2/1994 | Apelian et al. | 585/533 |
| 5,362,697 A | 11/1994 | Fung et al. | 502/71 |
| 5,849,960 A | 12/1998 | Singleton et al. | 568/909 |
| 6,077,498 A | 6/2000 | Diaz Cabanas et al. | 423/702 |

FOREIGN PATENT DOCUMENTS

| | | |
|---|---|---|
| EP | 0293032 | 5/1988 |
| EP | 0311 310 B1 * | 5/1992 |
| WO | WO 97/17290 | 5/1997 |

OTHER PUBLICATIONS

Industrial Chemicals, Third Edition, pp. 60-62, W.L. Faith et al., John Wiley & Sons, Inc., date unknown.

* cited by examiner

*Primary Examiner*—In Suk Bullock
(74) *Attorney, Agent, or Firm*—Andrew B. Griffis

(57) ABSTRACT

In a process for oligomerizing a $C_2$ to $C_6$ n-olefin feedstock over surface deactivated ZSM-23, the feedstock contains from about 0.1 wt % to about 25 wt % of an iso-olefin and the $C_{12}$+ fraction of the oligomerized olefin product contains less than 0.5 atom % of quaternary carbon atoms.

21 Claims, No Drawings

OLEFIN OLIGOMERIZATION PROCESS

CROSS REFERENCE TO RELATED APPLICATIONS

This application is a National Stage Application of International Application No. PCT/US03109733, filed Mar. 28, 2003, which claims the benefit of Provisional Application No. 60/368,927, filed Mar. 29, 2002. These applications are incorporated herein by reference.

FIELD

This invention relates to a process for oligomerizing a lower molecular weight olefin to produce a higher molecular weight olefin mixture, more specifically a substantially linear olefinic hydrocarbon mixture.

BACKGROUND

Long chain olefins ($C_{10}+$) are important starting materials in the production of sulfonate surfactants, in which the olefins are used to alkylate aromatic hydrocarbons and the resultant alkyl aromatics are sulfonated to produce alkylaryl sulfonates. In addition, the alcohols of long chain olefins have considerable commercial importance in a variety of applications, including detergents, soaps, surfactants, and freeze point depressants in lubricating oils. In such applications, it is important that the olefins employed are substantially free of quaternary carbon atoms because materials containing quaternary carbon atoms are resistant to biodegradation.

One potential route for the production of long chain olefins is by the oligomerization of lower ($C_2$ to $C_6$) olefins, typically using an acidic catalyst, such as a zeolite. Thus, for example, it is known from U.S. Pat. Nos. 3,960,978, 4,150,062; 4,211,640; 4,227,992; and 4,547,613 to oligomerize lower olefins over ZSM-5.

U.S. Pat. Nos. 4,855,527; 4,870,038 and 5,026,933 describe a process for producing high molecular weight, slightly branched hydrocarbon oligomers from a lower olefin feedstock employing a shape selective crystalline silicate catalyst, ZSM-23, which has been surface deactivated. The resultant oligomer mixture comprises at least 20% by weight of olefins having at least 12 carbon atoms and an average of from 0.8 to 2.0 branches per carbon chain.

U.S. Pat. No. 5,284,989 is directed to a process for producing substantially linear hydrocarbons by oligomerizing a lower olefin at elevated temperature and pressure in the presence of an acidic aluminosilicate zeolite selected from ZSM-22, ZSM-23 and ZSM-35 which has been surface-deactivated by contacting with oxalic acid.

In view of the need to avoid the production of quaternary carbon atoms in the resultant olefin oligomers, it is normal to employ oligomerization feeds which consist essentially of n-olefins and which are substantially free of iso-olefins, such as iso-butylene and iso-amylene. This poses a problem in that one source of lower olefins in a modern integrated oil refinery is the unreacted effluent stream from the MTBE (methyl tertiary butyl ether) production unit, which stream inherently contains up to 5 wt % of iso-butylene. Thus, existing oligomerization processes either avoid the use of the MTBE effluent feed or else require expensive purification steps to remove the iso-olefins.

In accordance with the invention, it has now surprisingly been found that, when surface deactivated ZSM-23 is used to oligomerize a lower olefin feed containing significant quantities of iso-olefins, such as the unreacted effluent from an MTBE unit, the $C_{12}+$ product is substantially free of quaternary carbon atoms. Instead, it is found that any quaternary carbon-containing materials are concentrated in the $C_8$ fraction, which can then be removed for use as a high-octane gasoline product. Although the reason for this desirable result is not fully understood, it is believed that the size of the pores of the ZSM-23 are such that, although iso-butylene can enter the pores to react with, for example, n-butylene, the resultant branched $C_8$ oligomer is too large to access the pores for further reaction.

SUMMARY

Accordingly, the invention resides in a first aspect in an olefin oligomerization process comprising:
(a) contacting a feedstock comprising one or more $C_2$ to $C_6$ n-olefins and from about 0.1 wt % to about 25 wt % of an iso-olefin under oligomerization conditions with surface-deactivated ZSM-23 to produce an oligomerized olefin product; and
(b) separating from said oligomerized olefin product a $C_{12}+$ fraction containing less than 0.5 atom % of quaternary carbon atoms.

In one embodiment, said feedstock contains about 0.5 wt % to about 5 wt % of said iso-olefin.

Typically, said iso-olefin is selected from iso-butylene and iso-amylene.

Conveniently, the n-olefin in the feedstock is selected from propylene, n-butene and mixtures thereof.

In one embodiment, the feedstock is the unreacted effluent stream from an MTBE unit.

Conveniently, the feedstock contains less than 100 ppm of dimethyl ether and has a sulfur content of less than 10 ppm.

Conveniently, the ZSM-23 has been surface deactivated with a sterically hindered nitrogenous base, such as 2,4,6-collidine.

In a second aspect, the invention resides in a process for producing a long chain alcohol mixture comprising contacting said $C_{12}+$ fraction with carbon monoxide and hydrogen under hydroformylation conditions and in the presence of a hydroformylation catalyst.

In a third aspect, the invention resides in a process for producing an alkylaromatic compound comprising contacting an aromatic compound with said $C_{12}+$ fraction under alkylation conditions and in the presence of an alkylation catalyst.

In a fourth aspect, the invention resides in a process for preparing an alkylaryl sulfonate by sulfonating the alkylaromatic compound produced in accordance with said third aspect of the invention.

DETAILED DESCRIPTION OF THE EMBODIMENTS

The present invention provides an improved process for producing slightly branched, high molecular weight olefinic hydrocarbons by oligomerizing a lower olefinic hydrocarbon feedstock in the presence of a surface-deactivated ZSM-23 catalyst. The use of such a catalyst is found, unexpectedly, to allow the use of an olefin feedstock that contains significant quantities of iso-olefins, such as isobutylene, without producing deleterious quantities of quaternary carbon atoms in the $C_{12}+$ fraction.

The olefinic hydrocarbon feedstock used in the process of the invention comprises one or more $C_2$ to $C_6$ n-olefins, such as propane and/or n-butene. In addition, the feedstock contains about 0.1% to about 25%, such as about 0.5% to 5% of an iso-olefin by weight of the total feedstock. Typically, the iso-olefin will be iso-butylene and/or iso-amylene. One preferred olefinic feedstock for use in the process of the invention is the unreacted effluent stream from an MTBE production unit, which stream typically contains n-butene together with iso-butylene in amounts up to 5 wt %. A practical feedstock, such as an MTBE effluent, may also contain dimethyl ether and sulfur impurities. If present, the dimethyl ether content is preferably less than 100 ppm and the sulfur content is preferably less than 10 ppm.

The olefinic hydrocarbon feedstock can also contain low molecular weight, typically $C_4$-$C_6$, saturated hydrocarbons, typically in amounts between about 5% and about 70% by weight of the overall feedstock.

The oligomerization catalyst used in the process of the invention comprises ZSM-23 which has been surface deactivated, typically by treatment with a sterically hindered nitrogenous base, such as a trialkyl pyridine compound, and preferably with 2,4,6-collidine (2,4,6-trimethyl pyridine, gamma-collidine). The surface deactivating compound should have a minimum cross-sectional diameter greater than the effective pore size of the zeolite to be treated; i.e., greater than 5 Angstroms. ZSM-23 and its characteristic X-ray diffraction pattern are described in detail in U.S. Pat. No. 4,076,842. Preferably, the ZSM-23 employed in the catalyst has an alpha value of about 25 and a crystal size of less than 0.1 micron and is conveniently composited with a binder, such as alumina.

Suitable oligomerization conditions include a temperature of about 160° C. to about 250° C., such as about 190° C. to about 230° C., for example about 210° C. to about 220° C.; a pressure in the range of about 500 psig (3447 kPa (gauge)) to about 1500 psig (10342 kPa (gauge)), such as in the range of about 750 psig (5171 kPa (gauge)) to about 1250 psig (8618 kPa (gauge)), and a feed weight hour space velocity (WHSV) in the range of about 0.1 $hr^{-1}$ to about 4.0 $hr^{-1}$, such as in the range of about 0.2 $hr^{-1}$ to about 3.0 $hr^{-1}$, for example in the range of about 1.75 $hr^{-1}$ to about 2.25 $hr^{-1}$.

Where surface deactivation is achieved by treatment with a trialkyl pyridine compound, the feed to the oligomerization process can include additional trialkyl pyridine compound so that the surface properties of the zeolite are maintained during the process. Further details of the oligomerization process can be found in U.S. Pat. No. 5,026,933.

The product of the oligomerization process of the invention is an olefinic hydrocarbon mixture which comprises at least 5 wt %, such as at least 20 wt %, for example at least 85 wt % of mono-olefin oligomers of the empirical formula:

$$C_nH_{2n}$$

wherein n is greater than or equal to 6 and wherein said mono-olefin oligomers comprise at least 20 wt %, and conveniently at least 60 wt %, of olefins having at least 12 carbon atoms and said olefins having at least 12 carbon atoms ($C_{12}$+ olefins) have an average of from about 0.8 to about 2.0, such as from about 0.8 to about 1.3, $C_1$-$C_3$ alkyl branches per carbon chain. Conveniently, the olefins having at least 12 carbon atoms contain no branches other than methyl and ethyl groups.

In particular it is found that, despite the presence of iso-olefins in the oligomerization feed, the $C_{12}$+ olefinic product of the present process contains less than 0.5 atom %, of quaternary carbon atoms. As previously stated, although the reasons for the low quaternary carbon content of the $C_{12}$+ olefinic product are not fully understood, it is believed that the size of the pores of the ZSM-23 are such that, although iso-butylene can enter the pores to react with, for example, n-butylene, the resultant branched $C_8$ oligomer is too large to access the pores for further reaction. Thus the iso-olefin reaction products are concentrated, in the case of a $C_4$ olefin feed, in the $C_8$ fraction. Because such a fraction inherently has a high octane value, it is advantageous to remove this fraction from the oligomerization product for use as a gasoline blending component.

The percentage of quaternary carbon atoms in the $C_{12}$+ olefinic product is conveniently determined by the $^{13}C$—NMR technique described in U.S. Pat. No. 5,849,960 at column 4, line 23 to column 5, line 3 and in particular the J-Modulated Spin Echo NMR technique (JMSE) using a ½J delay of 4 ms and incorporating the DEPT-135 NMR correction.

The lightly branched $C_{12}$+ olefinic hydrocarbon fraction from the oligomerization process of the invention is conveniently used in the production of long chain alcohols for application as, for example, detergents, soaps, surfactants, and freeze point depressants in lubricating oils. Typically this is achieved by hydroformylation, that is reaction with carbon monoxide and hydrogen, according to the Oxo process. Catalysts employed can be cobalt or rhodium which may be modified with phosphine, phosphite, arsine or pyridine ligands, as described in U.S. Pat Nos. 3,231,621; 3,239,566; 3,239,569; 3,239,570; 3,239,571; 3,420,898; 3,440,291; 3,448,158; 3,448,157; 3,496,203; and 3,496,204; 3,501,515; and 3,527,818.

Typical hydroformylation reaction conditions include a temperature of about 125° C. to about 200° C., a pressure of about 2170 kPa to about 32550 kPa (300 psig to 4000 psig) and a catalyst to olefin ratio of about 1:5000 to about 1:1. The molar ratio of hydrogen to carbon monoxide is usually about 0.5 to about 10, such as about 1 to about 2. The hydroformylation reaction typically produces an aldehyde which can then be hydrogenated to generate the required alcohol product.

The hydroformylation process can be carried out in the presence of an inert solvent, such as a ketone, e.g., acetone, methyl ethyl ketone, methyl isobutyl ketone, acetophenone, and cyclohexanone; an aromatic compound, e.g., benzene, toluene and the xylenes; a halogenated aromaic compound, e.g., chlorobenzene and orthodichlorobenzene; a halogenated paraffinic hydrocarbon, e.g., methylene chloride and carbon tetrachloride; a paraffin, e.g., hexane, heptane, methylcyclohexane and isooctane, and a nitrile, e.g., such as benzonitrile and acetonitrile.

The catalyst ligand may be made of tertiary organo phosphines, such as trialkyl phosphines, triamyl phosphine, trihexyl phosphine, dimethyl ethyl phosphine, diamylethyl phosphine, tricyclopentyl (or hexyl) phosphine, diphenyl butyl phosphine, dipenyl benzyl phosphine, triethoxy phosphine, butyl diethyoxy phosphine, triphenyl phosphine, dimethyl phenyl phosphine, methyl diphenyl phosphine, dimethyl propyl phosphine, the tritolyl phosphines and the corresponding arsines and stibines. Included as bidentate-type ligands are tetramethyl diphosphinoethane, tetramethyl diphosphinopropane, tetraethyl diphosphinoethane, tetrabutyl diphosphinoethane, dimethyl diethyl diphosphinoethane, tetraphenyl diphosphinoethane, tetraperfluorophenyl diphosphinoethane, tetraphenyl diphosphinopropane, tetraphenyl diphosphinobutane, dimethyl diphenyl diphosphinoethane, diethyl diphenyl diphosphinopropane and tetratrolyl diphosphinoethane.

Examples of other suitable ligands are the phosphabicyclohydrocarbons, such as 9-hydrocarbyl-9-phosphabicyclononane in which the smallest P-containing ring contains at least 5 carbon atoms. Some examples include 9-aryl-9-phosphabicyclo[4.2.1]nonane, (di)alkyl-9-aryl-9-phosphabicyclo [4.2.1]nonane, 9-alkyl-9-phosphabicyclo[4.2.1]nonane, 9-cycloalkyl-9-phosphabicyclo[4.2.1]nonane, 9-cycloalkenyl-9-phosphabicyclo[4.2.1]nonane, and their [3.3.1] and [3.2.1] counterparts, as well as their triene counterparts.

Alternatively, the lightly branched $C_{12}+$ olefinic hydrocarbon fraction from the oligomerization process of the invention can be used, either alone or in admixture with linear alpha-olefins, as an alkylating agent in a process for the selective alkylation of an aromatic compound (e.g., benzene) with a relatively long chain length alkylating agent to produce substantially linear phenylalkanes. The alkylation process is conducted such that the organic reactants, i.e., the aromatic compound and the olefinic hydrocarbon mixture, are contacted under effective alkylation conditions with a suitable acid catalyst. Suitable aromatic hydrocarbons include benzene, toluene, xylene and naphthalene, with preferred compounds being benzene and toluene.

In one embodiment, the catalyst is a homogeneous acid catalyst such as a Lewis acid catalyst, for example aluminum chloride. Alternatively, the homogeneous acid catalyst is a Brønsted acid catalyst such as HF or phosphoric acid. Suitable alkylation conditions with a homogeneous catalyst include a temperature of from about −10° C. to about 100° C., a pressure of from about 100 kPa to about 2500 kPa (1.0 to 25 atmospheres), a feed weight hourly space velocity (WHSV) of from about 0.2 $hr^{-1}$ to about 10 $hr^{-1}$ and an aromatic compound to olefinic hydrocarbon mixture mole ratio of from about 1:1 to about 15:1. Typical reaction conditions include a temperature of from about 0° C. to about 50° C., a pressure of from about 100 kPa to about 300 kPa (1.0 to about 3.0 atmospheres), a feed weight hourly space velocity (WHSV) of from about 0.1 $hr^{-1}$ to about 0.5 $hr^{-1}$ and an aromatic compound to olefinic hydrocarbon mixture mole ratio of from about 5:1 to about 10:1. The reactants can be in either the vapor phase or the liquid phase and can be neat, i.e., free from intentional admixture or dilution with other material, or they can be brought into contact with the catalyst composition with the aid of carrier gases or diluents such as, for example, hydrogen or nitrogen.

In a further embodiment, the alkylation process is conducted in the presence of a heterogeneous catalyst, such as a molecular sieve. Suitable molecular sieves include mordenite, particularly dealuminized mordenite and other 6-7 Angstrom pore molecular sieves disclosed in U.S. Pat. No. 5,026,933.

In one practical embodiment, the alkylation catalyst comprises a molecular sieve having an X-ray diffraction pattern including d-spacing maxima at 12.4±0.25, 6.9±0.15, 3.57±0.07 and 3.42±0.07 Angstroms. The X-ray diffraction data used to characterize said molecular sieve are obtained by standard techniques using the K-alpha doublet of copper as the incident radiation and a diffractometer equipped with a scintillation counter and associated computer as the collection system. Materials having the required X-ray faction lines are sometimes referred to as molecular sieves of the MCM-22 family and include MCM-22 (described in U.S. Pat. No. 4,954,325), PSH-3 (described in U.S. Pat. No. 4,439,409), SSZ-25 (described in U.S. Pat. No. 4,826,667), ERB-1 is described in European Patent No. 0293032, ITQ-1 is described in U.S. Pat. No. 6,077,498, ITQ-2 is described in International Patent Publication No. WO97/17290, MCM-36 (described in U.S. Pat. No. 5,250,277), MCM-49 (described in U.S. Pat. No. 5,236,575) and MCM-56 (described in U.S. Pat. No. 5,362,697).

The molecular sieve alkylation catalyst can be combined in conventional manner with an oxide binder, such as alumina, such that the final alkylation catalyst contains between about 2 and about 80 wt % sieve.

With a molecular sieve catalyst, suitable alkylation conditions include a temperature of from about 0° C. to about 500° C., a pressure of from about 20 kPa to about 25000 kPa (0.2 to 250 atmospheres), a feed weight hourly space velocity (WHSV) of from about 0.1 $hr^{-1}$ to about 500 $hr^{-1}$, and an aromatic compound to olefinic hydrocarbon mixture mole ratio of from about 1:1 to about 20:1. The WHSV is based upon the weight of the catalyst composition employed, i.e., the total weight of active catalyst (and binder if present). Typical reaction conditions include a temperature within the range of from about 100° C. to about 350° C., a pressure of from about 100 kPa to about 2500 kPa (1 to 25 atmospheres), a WHSV of from about 0.5 $hr^{-1}$ to about 100 $hr^{-1}$ and an aromatic compound to olefinic hydrocarbon mixture mole ratio of from about 4:1 to about 15:1. Again, the reactants can be in either the vapor phase or the liquid phase and can be neat, i.e. free from intentional admixture or dilution with other material, or they can be brought into contact with the zeolite catalyst composition with the aid of carrier gases or diluents such as, for example, hydrogen or nitrogen.

The alkylation process of the invention produces an alkylaromatic hydrocarbon mixture in which the alkyl side chains are lightly branched and have less tan 0.5 atom % of quaternary carbon atoms and in which most of the aromatic species are located at the 2- or 3-position in the alkyl side chain. The alkylaromatic hydrocarbon mixture is therefore particularly useful as an intermediate in the production of alkylarylsulfonates, which are useful as detergents or surfactants. Processes for sulfonating alkylbenzenes are described in the U.S. Pat. No. 4,298,547. More particularly, alkylaromatic hydrocarbons may be converted to alkylarylsulfonates by sulfonation of the aromatic ring with sulfuric acid. The sulfonation reaction is well known in the art and is commonly carried out by contacting the organic compound with sulfuric acid at temperatures of from about −70° C. to about +60° C. Detailed descriptions of specific commercial processes abound the literature. See, for instance, pages 60-62 of INDUSTRIAL CHEMICALS, Third Edition, by W. L. Faith et al, published by John Wiley & Sons, Inc.

The invention claimed is:

1. An olefin oligomerization process comprising:
   (a) contacting a feedstock comprising one or more $C_2$ to $C_6$ n-olefins and from about 0.5 wt % to about 25 wt % of an iso-olefin under oligomerization conditions with surface-deactivated ZSM-23 to produce an oligomerized olefin product;
   (b) separating from said oligomerized olefin product a $C_{12}+$ fraction containing less than 0.5 atom % of quaternary carbon atoms and including $C_{12+}$ oligomers having ethyl side groups; and
   (c) isolating a $C_8$ fraction having a higher concentration of quaternary carbon atoms than said $C_{12+}$ fraction.

2. The process according to claim 1, wherein said feedstock contains 0.5 wt % to about 5 wt % of an iso-olefin.

3. The process according to claim 1, wherein said iso-olefin is iso-butylene and/or iso-amylene.

4. The process according to claim 1, wherein said one or more n-olefins in the feedstock are selected from propylene, n-butene and mixtures thereof.

5. The process according to claim 1, wherein said feedstock is the unreacted effluent stream from an MTBE unit.

6. The process according to claim 1, wherein said feedstock contains less than 100 ppm of dimethyl ether, and a sulfur content of less than 10 ppm.

7. The process according to claim 1, wherein said ZSM-23 has been surface deactivated with a sterically hindered nitrogenous base.

8. The process according to claim 7, wherein said sterically hindered nitrogenous base is 2,4,6-collidine.

9. The process according to claim 1, wherein said oligomerization conditions include a temperature of about 160 to about 250° C.

10. The process according to claim 1, wherein said oligomerization conditions include a temperature of about 190 to about 230° C.

11. The process according to claim 1, wherein said oligomerization conditions include a temperature of about 210 to about 220° C.

12. The process according to claim 1, wherein said oligomerization conditions comprise a pressure in the range of from about 500 psig (3447 kPa (gauge)) to about 1500 psig (10342 kPa (gauge)).

13. The process according to claim 1, wherein said oligomerization conditions comprise a pressure in the range of from about 750 psig (5171 kPa (gauge)) to about 1250 psig (8618 kPa (gauge)).

14. The process according to claim 1, wherein said oligomerization conditions comprise a weight hourly space velocity of from about 0.1 $hr^{-1}$ to about 4.0 $hr^{-1}$.

15. The process according to claim 1, wherein said oligomerization conditions comprise a weight hourly space velocity of from about 0.2 $hr^{-1}$ to about 3.0 $hr^{-1}$.

16. The process according to claim 1, wherein said $C_{12}+$ fraction has an average of from about 0.8 to about 2.0 $C_2$-$C_3$ alkyl branches per carbon chain.

17. The process according to claim 1, wherein said $C_{12}+$ fraction has an average of from about 0.8 to about 1.3 $C_2$-$C_3$ alkyl branches per carbon chain.

18. A method for producing a long chain alcohol mixture comprising contacting the $C_{12}+$ fraction produced by the process of claim 1 with carbon monoxide and hydrogen under hydroformylation conditions and in the presence of a hydroformylation catalyst.

19. A method for producing an alkylaromatic compound comprising contacting an aromatic compound with the $C_{12}+$ fraction produced by the process of claim 1 under alkylation conditions and in the presence of an alkylation catalyst.

20. A method for preparing an alkylaryl sulfonate by sulfonating the alkylaromatic compound produced by the method of claim 19.

21. An olefin oligomerization process comprising:
(a) contacting a feedstock comprising one or more $C_2$ to $C_6$ n-olefins and from about 0.5 wt % to about 25 wt % of an iso-olefin under oligomerization conditions with surface-deactivated ZSM-23 to produce an oligomerized olefin product including at least one iso-olefin reaction product and at least one $C_{12+}$ reaction product having ethyl side groups; and
(b) separating from said oligomerized olefin product said at least one $C_{12+}$ reaction product, wherein said at least one $C_{12+}$ reaction product is characterized as containing less than 0.5 atoms % of quaternary carbon atoms;
(c) obtaining a $C_{12-}$ reaction product having a higher concentration of quaternary carbon atoms than said at least one $C_{12+}$ reaction product from step (b).

* * * * *